United States Patent [19]

Barber

[11] 4,110,177

[45] Aug. 29, 1978

[54] PROCESS FOR RECOVERY AND PURIFICATION OF A PERFLUOROCARBOXYLIC ACID FLUORIDE FROM ELECTROCHEMICAL CELL FLUORINATION EFFLUENT

[75] Inventor: Franklin T. Barber, Bartlesville, Okla.

[73] Assignee: Phillips Petroleum Company, Bartlesville, Okla.

[21] Appl. No.: 852,162

[22] Filed: Nov. 16, 1977

[51] Int. Cl.$^2$ ............................................. C25B 3/08
[52] U.S. Cl. ..................................... 204/59 F; 203/42
[58] Field of Search ................. 210/69, 73 R; 203/42, 203/71; 204/59 F

[56] References Cited

U.S. PATENT DOCUMENTS

| 2,711,826 | 6/1955 | Young et al. ......................... 210/69 |
| 4,025,567 | 5/1977 | Hutchinson et al. ................. 203/42 |
| 4,029,552 | 6/1977 | Fozzard ................................ 203/71 |

Primary Examiner—R. L. Andrews

[57] ABSTRACT

A recovery and purification operation in which a perfluorocarboxylic acid fluoride, e.g., trifluoroacetylfluoride, is recovered having a high purity from an electrochemical cell fluorination operation is described. The effluent is compressed and chilled, separation of vapor from liquid phases is effected to produce a liquid which is further chilled and subcooled and employed as absorption medium in an absorption zone. Vapors separated are compressed and chilled and subjected to a further phase separation, vapors from which are passed to the absorption zone. The enriched absorption medium together with liquid from the second phase separation is passed to a fractionation zone for recovery of the perfluorocarboxylic acid fluoride from incompletely fluorinated compounds which can be returned to the cell for further fluorination.

The invention is applicable to the recovery of perfluorocarboxylic acid fluorides of mono- and dicarboxylic acids containing from 2 to about 10 carbon atoms.

10 Claims, 1 Drawing Figure

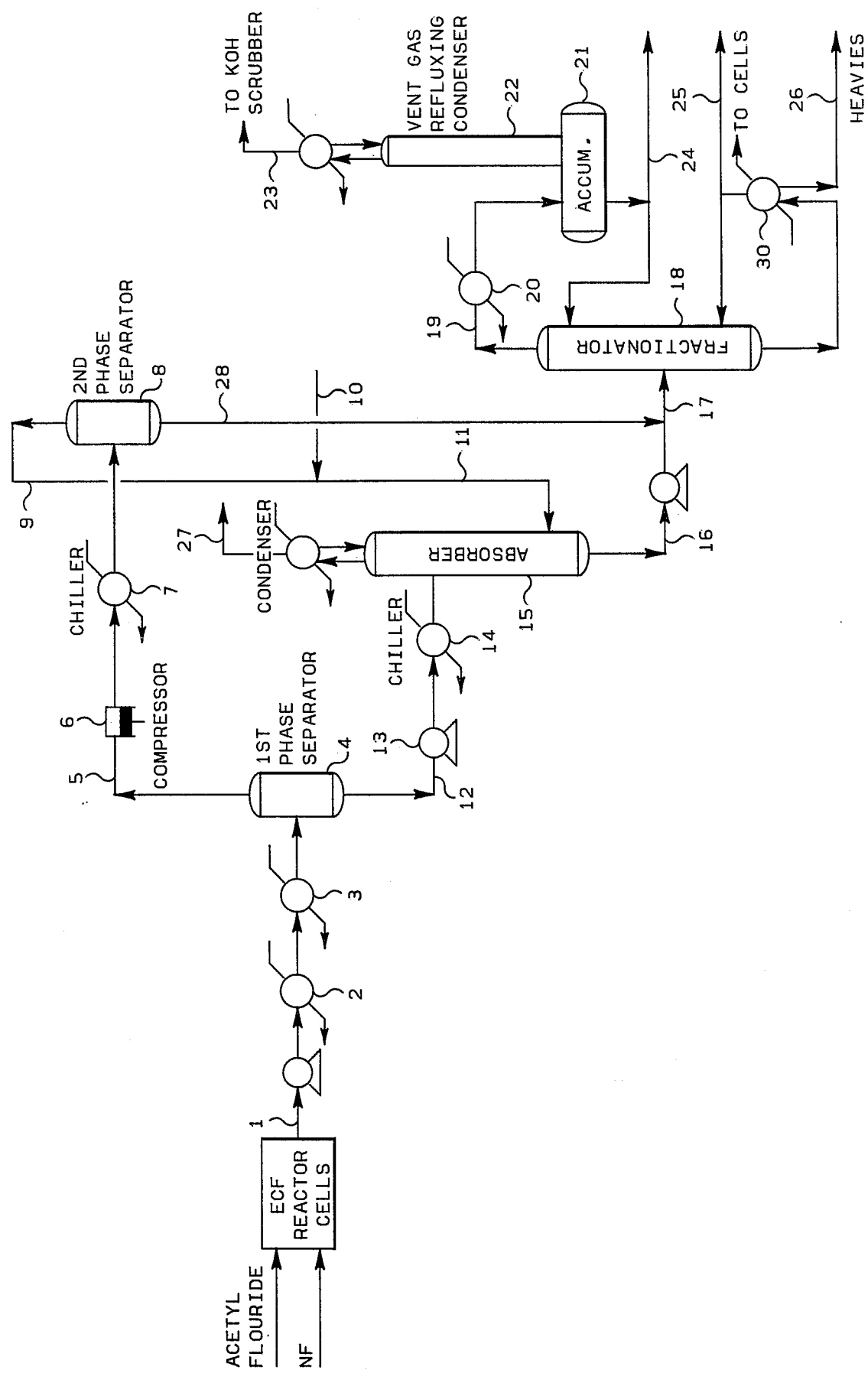

PROCESS FOR RECOVERY AND PURIFICATION OF A PERFLUOROCARBOXYLIC ACID FLUORIDE FROM ELECTROCHEMICAL CELL FLUORINATION EFFLUENT

This invention relates to the recovery and purification of perfluorocarboxylic acid fluoride from electrochemical cell effluent. In one of its aspects it relates to a combination of steps involving compression and chilling and phase separation.

In one of its concepts, the invention provides in a series of steps involving compression, chilling, and phase separation the use of a separated liquid in subcooled condition as in absorption medium for absorbing for later fractionation vapors obtained from a second phase separation practiced upon compressing and chilling vapors from the first phase separation. In another of its concepts, the invention provides, in the operation of the fractionation zone, for the use of an overhead accumulator in combination with the vent gas refluxing condenser to obtain the desired product, e.g. trifluoroacetylfluoride and as a bottoms product a vaporous stream, as obtained from a reboiler zone, containing incompletely fluorinated compounds which can be returned to the cell for further fluorination.

The invention is applicable to the recovery of perfluorocarboxylic acid fluorides of mono- and dicarboxylic acids containing from about 2 to about 10 carbon atoms. The completely fluorinated products of such acids as acetic acid, propionic acid, 3-methyl butyric acid, succinic acid, valeric acid, adipic acid, decanoic acid can be separated by a method according to the claimed invention.

Thus, this invention is concerned with the recovery and purification of perfluorocarboxylic acid fluoride from electrochemical cell effluent in preparation for a subsequent metathesis to perfluorocarboxylic acid. The invention is distinguished by its simplicity. The invention is now further described in connection with production of trifluoroacetylfluoride.

Other than phase separators, only three separation steps are required to isolate fixed gases and other waste products, the trifluoroacetylfluoride product, and the unreacted acetylfluoride and partially fluorinated acetylfluorides for recycle to the electrochemical fluorination cells. A key step is effected in the acetylfluoride absorber wherein the less volatile acetylfluoride, partially fluorinated acetylfluorides and dissolved HF are chilled to about −100° F. (−73° C.) under pressure of about 195 psia (1.34 MPa) and used as an absorbent to recover the less volatile trifluoroacetylfluoride which has remained uncondensed at −85° F. (−65° C.) and 245 psia (1.69 MPa). The second important step is the acetylfluoride fractionator which provides a vent gas absorber for conservation of trifluoroacetylfluoride. In the bottom of the fractionator the primary bottom product is removed as a vapor and heavies are removed as a liquid. The features of the fractionator, however, are not broadly novel.

An object of this invention is to provide for the simplified recovery and purification of a perfluorocarboxylic acid fluoride from an electrochemical cell fluorination operation effluent. Another object of this invention is to provide a combination of compression, chilling, phase separation, absorption and fractionation steps so arranged in combination as to provide for more efficient use of the energy of refrigeration and compression.

Other aspects, concepts, objects and the several advantages of the invention are apparent from a study of this disclosure, the drawing and the appended claims.

According to the present invention there is provided a method for the recovery of a perfluorocarboxylic acid fluoride, e.g., trifluoroacetylfluoride, in connection with which it will now be described, from a reaction mass stream from an electrochemical fluorination zone in which electrochemical fluorination of acetylfluoride to produce trifluoroacetylfluoride is effected which comprises: chilling said stream under pressure to condense a substantial portion of the constituents thereof, passing the chilled stream into a phase separation zone, in said zone separating said stream into at least a first vaporous stream and a first liquid stream, removing vapors from said zone, compressing, chilling and passing the same into a second zone, in said second zone separating at least one further vaporous stream from at least one further liquid stream, further chilling said first liquid stream to subcool the same and then passing it into an absorption zone as an absorption medium therefor, passing said further vaporous stream from said second zone into said absorption zone into absorption contact with said first liquid stream therein to recover into said medium substantial quantities of trifluoroacetylfluoride, other reaction products and HF therefrom, removing thus enriched absorption medium from said absorption zone and subjecting the same to fractionation in a fractionation zone to recover the trifluoroacetylfluoride therefrom.

According to the invention, the said further liquid stream can be passed into the fractionation zone directly as obtained from said second phase separation.

In the drawing, there is shown diagrammatically a flow plan according to the invention in which use is made of the first separated liquid to recover remaining feed and products in the vapors of the operation which remain as such following a second phase separation. This is to be compared with the otherwise needed significantly more compression and deeper refrigeration to lower temperatures, heretofore needed.

Acetylfluoride and hydrogenfluoride are subjected to electrochemical fluorination to produce an effluent 1. Reference is now made to the following calculated material balance table for the analysis of the several operational streams now being considered.

TABLE

| Stream No. | 1 | 5 | 9 | 10 | 11 | 12 | 16 | 17 | 23 | 24 | 25 | 26 | 27 | 28 |
|---|---|---|---|---|---|---|---|---|---|---|---|---|---|---|
| Material Balance, kg Mols/Day | | | | | | | | | | | | | | |
| $H_2$ | 164.0 | 163.9 | 160.7 | | 160.7 | 0.1 | 3.4 | 6.6 | 6.5 | Trace | Trace | Trace | 157.4 | 3.2 |
| $CF_4$ | 5.8 | 5.7 | 3.1 | | 3.1 | 0.1 | 0.9 | 3.6 | 3.5 | 0.1 | Trace | Trace | 2.2 | 2.7 |
| $COF_2$ | 4.7 | 4.6 | 1.0 | | 1.0 | 0.1 | 0.9 | 4.4 | 3.8 | 0.7 | Trace | Trace | 0.3 | 3.6 |
| $C_2F_6$ | Trace | Trace | Trace | | Trace | Trace | Trace | Trace | Trace | Trace | Trace | Trace | Trace | Trace |
| $CF_3COF$ | 45.8 | 42.5 | 1.9 | 6.7 | 8.6 | 3.3 | 11.1 | 51.7 | 0.6 | 50.7 | 0.4 | Trace | 0.7 | 40.6 |
| $CHF_2COF$ | 85.4 | 46.9 | 0.1 | | 0.1 | 38.5 | 38.1 | 84.9 | Trace | Trace | 84.8 | 0.1 | 0.5 | 46.8 |
| HF | 109.0 | 43.2 | 0.1 | | 0.1 | 65.8 | 65.3 | 108.4 | Trace | Trace | 108.2 | 0.2 | 0.6 | 43.1 |
| $CH_3COF$ | 63.3 | 21.9 | Trace | 6.9 | 6.9 | 41.4 | 48.1 | 70.0 | Trace | Trace | 69.8 | 0.1 | 0.2 | 21.9 |
| $CH_2FCOF$ | 50.0 | 5.5 | Trace | | Trace | 44.5 | 44.5 | 50.0 | Trace | Trace | 49.8 | 0.2 | Trace | 5.5 |
| $CO_2$ | 0.0 | 0.0 | 0.0 | 10.7 | 10.7 | 0.0 | 7.6 | 7.6 | 7.1 | 0.5 | Trace | Trace | 3.0 | 0.0 |

TABLE-continued

| Stream No. | Material Balance, kg Mols/Day | | | | | | | | | | | | | |
|---|---|---|---|---|---|---|---|---|---|---|---|---|---|---|
| | 1 | 5 | 9 | 10 | 11 | 12 | 16 | 17 | 23 | 24 | 25 | 26 | 27 | 28 |
| | 528.0 | 334.2 | 166.9 | 24.3 | 191.2 | 193.8 | 219.9 | 387.2 | 21.5 | 52.0 | 313.0 | 0.6 | 164.9 | 167.4 |

Effluent 1 is compressed and chilled in chillers 2 and 3, thus being partially condensed in two stages to about 20° F. (−7° C.) at 15 psia (0.10 MPa). Phases formed are separated in first phase separator 4.

Vapor separated in phase separator 4 is passed by 5 compressed in 6 and chilled in 7 to about −85° F. (−65° C.) at 245 psia (1.69 MPa) and passed into a second phase separator 8 from which separated vapor is passed by 9, together with $CF_3COF$ and $CH_3COF$ in 10 via 11 to absorber 15.

Liquid from first phase separator 4 is passed by 12 pump 13 and chiller 14 to absorber 15 at −100° F. (−73° C.) and 195 psia (1.34 MPa) to yield an overhead 27 largely consisting of hydrogen and carbon dioxide and a bottoms stream 16 containing important quantities of $CHF_2COF$, HF, $CH_3COF$, and $CH_2FCOF$.

Stream 16 is passed together with bottoms stream 28 from the second phase separator 8 into a fractionator 18 via 17. In fractionator 18 a separation is performed to recover trifluoroacetylfluoride as stream 24, stream 25 consisting largely of difluoroacetylfluoride, HF, acetylfluoride and monofluoroacetylfluoride for return to the cell. A heavies stream 26 is removed from the operation.

The vapors from fractionator 18 are treated as follows. These are passed by 19 and chiller 20 into accumulator 21 from which the vapor passes through a vent gas absorber 22 equipped with a refluxing condenser operating at about −70° F. (−57° C.). Uncondensed absorber vapor passes by 23 to a KOH scrubber.

Owing to the operation of reboiler 30 it will be noted that stream 25 is essentially vaporous.

Returning to absorber 15, vapors passing through the condenser are passed by 27 to a KOH scrubber for final removal of fluorine compounds. The condenser is operated at about −120° F. (−86° C.).

The fractionator 18 is operated at 245 psia (1.69 MPa). The overhead accumulator has a temperature of 44° F. (7° C.).

The completely fluorinated acetylfluoride, i.e., trifluoroacetylfluoride, $CF_3COF$, is obtained at 24 from the accumulator at a purity of 98.9 mole percent.

It will be seen that the operation neatly performs the needed recovery of product and materials to be recycled to the cell, as well as separation of impurities, with a minimum of needed compressing and refrigeration.

Calculated Example

Effluent from an electrochemical fluorination reactor in which acetylfluoride is reacted with HF is compressed, cooled and partially condensed in two stages to about 20° F. (−7° C.) and 15 psia (0.10 MPa) and formed phases are separated. Liquid from the phase separator is pumped through a chiller and introduced into the top of the acetylfluoride absorber at −100° F. (−73° C.) and 195 psia (1.34 MPa). Phase separator vapor is compressed and chilled to −85° F. (−65° C.) and 245 psia (1.69 MPa) and passed to a second phase separator, vapor therefrom passing to the bottom of the absorber for recovery of uncondensed acetylfluorides. Final recovery of acetylfluoride is achieved with a small overhead condenser on the absorber operating at −120° F. (−86° C.). Vapor from the absorber, primarily hydrogen, carbon dioxide and carbon tetrafluoride, pass to a KOH scrubber for final removal of fluorine compounds. Absorber bottom product is combined with liquid from the second phase separator and fed to the acetylfluoride fractionator operating at 245 psia (1.69 MPa) and an overhead accumulator temperature of 44° F. (7° C.). Acetylfluoride is yielded as a liquid from the accumulator in 98.9 mole percent purity. Accumulator vapor passes to a vent gas absorber equipped with a refluxing condenser operating at −70° F. (−57° C.). Uncondensed absorber vapor passes to the KOH scrubber. Fractionator bottom product which is unconverted acetylfluoride, partially fluorinated acetylfluorides and HF, is yielded as a vapor from the fractionator reboiler for recycle to the electrochemical fluorination cells. Also yielded from the bottom of the column is a small purge stream of heavies which passes to waste disposal.

Reasonable variation and modification are possible within the scope of the foregoing disclosure, drawing and the appended claims to the invention the essence of which is that vapors separated from a first liquid-vapor separation effected on a stream containing a perfluorocarboxylic acid fluoride, derived from at least one of the acid fluorides of a mono- and a dicarboxylic acid, e.g., trifluoroacetylfluoride and by-products emanating from the electrochemical fluorination thereof are compressed, chilled and condensed providing upon further phase separation a liquid phase containing the desired product and a vapor stream from which recovery of perfluorocarboxylic acid fluoride and other materials is effected employing a liquid phase obtained in the first mentioned liquid phase separation as the absorption medium.

What is claimed is:

1. The recovery of trifluoroacetylfluoride from a reaction mass stream obtained from an electrochemical fluorination zone in which electrochemical fluorination of acetylfluoride to produce trifluoroacetylfluoride is effected which comprises: chilling said stream under pressure to condense a substantial portion of the constituents thereof, passing the chill stream into a phase separation zone, in said phase separation zone separating said stream into at least a first vapor stream and a first liquid stream, removing vapors from said zone, further chilling and passing the same into a second zone, in said second zone separating at least one further vaporous stream from at least one further liquid stream, pumping and chilling said first liquid stream to subcool the same and then passing it into an absorption zone as an absorption medium therefore, passing said further vaporous stream from said second zone into said absorption zone into absorption contact with said first liquid stream therein to recover into said medium substantial quantities of trifluoroacetylfluoride, other reaction products and HF therefrom, removing thus enriched absorption medium from said absorption zone and subjecting the same to fractionation in a fractionation zone to recover the trifluoroacetylfluoride therefrom.

2. The method of claim 1 wherein said further liquid stream is also passed into said fractionation zone.

3. The method of claim 1 wherein a stream containing trifluoroacetylfluoride, acetylfluoride and resulting from the metathesis of perfluorocarboxylic acid fluoride with a carboxylic acid to yield a carboxylic acid fluoride and perfluorocarboxylic acid is fed into said absorption zone.

4. The method of claim 1 wherein the overhead from said fractionation zone is chilled and passed to an accumulator zone from which a liquid phase separated therein is removed as product trifluoroacetylfluoride.

5. A method according to claim 4 wherein the vapors separating in said accumulator zone are subjected to a reflux condensing operation for recovery of additional liquid therefrom while a residual overhead is vented to appropriate further treatment as desired.

6. A method according to claim 1 wherein a liquid stream from the bottom portion of said fractionation zone is reboiled to produce a vaporous stream at least a portion of which is returned to the electrochemical fluorination zone.

7. A method according to claim 1 wherein the approximate conditions in the respective operations and places are of an order as follows:

|  | Degrees F. | psia |
|---|---|---|
| Feed to first phase separation zone | 20 | 15 |
| Second (phase separation) | −85 | 245 |
| Absorption medium fed to absorption zone | −100 | 195 |
| Absorption zone overhead | −120 | 195 |
| Feed to fractionation zone | −85 | 245 |
| Accumulator | 44 | 185 |
| Reflux condensing at accumulator | −70 | 184 |
| Fractionator bottom | 240 | 204 |

8. A method for the recovery of a perfluorocarboxylic acid fluoride derived from mono- and dicarboxylic acids containing from two to about ten carbon atoms according to the method of claim 1.

9. A method according to claim 8 wherein the perfluorocarboxylic acid fluoride is derived from at least one of the carboxylic acid fluorides of: acetic acid, propionic acid, 3-methyl butyric acid, succinic acid, valeric acid, adipic acid, decanoic acid.

10. The recovery of perfluorocarboxylic acid fluoride from a reaction mass stream obtained from an electrochemical fluorination zone in which electrochemical fluorination of an acid fluoride derived from a mono- and a dicarboxylic acid fluoride is effected which comprises: chilling said stream under pressure to condense a substantial portion of the constituents thereof, passing the chilled stream into a phase separation zone, in said phase separation zone separating said stream into at least a first vapor stream and a first liquid stream, removing vapors from said zone, further chilling and passing the same into a second zone, in said second zone separating at least one further vaporous stream from at least one further liquid stream, pumping and chilling said first liquid stream to subcool the same and then passing said further vaporous stream from said second zone into said absorption zone into absorption contact with said first liquid stream therein to recover into said medium substantial quantities of trifluorocarboxylic acid fluoride, other reaction products and HF therefrom, removing thus enriched absorption medium from said absorption zone and subjecting the same to fractionation in a fractionation zone to recover the trifluorocarboxylic acid fluoride therefrom.

* * * * *